United States Patent
Matsunae et al.

(10) Patent No.: US 6,217,644 B1
(45) Date of Patent: Apr. 17, 2001

(54) DENTAL ADHESIVE SET

(75) Inventors: Kaori Matsunae; Shoji Akahane, both of Tokyo (JP)

(73) Assignee: GC Corporation, Tokyo (JP)

( * ) Notice: Subject to any disclaimer, the term of this patent is extended or adjusted under 35 U.S.C. 154(b) by 0 days.

(21) Appl. No.: 09/379,573

(22) Filed: Aug. 24, 1999

(30) Foreign Application Priority Data

Aug. 9, 1998 (JP) .................................................. 10-254037

(51) Int. Cl.⁷ .......................... A61K 11/08; A61C 13/23
(52) U.S. Cl. ........................ 106/35; 523/116; 433/226; 433/228.1
(58) Field of Search .......................... 106/35; 523/116; 433/226, 228.1

(56) References Cited

U.S. PATENT DOCUMENTS

| 4,342,677 | 8/1982 | Muramatsu et al. | 523/116 |
|---|---|---|---|
| 4,374,936 | 2/1983 | Tomioka et al. | 523/116 |
| 4,524,824 | 6/1985 | Shimokobe et al. | 106/35 |
| 4,591,384 | 5/1986 | Akahane et al. | 106/35 |
| 4,632,824 | 12/1986 | Hirota et al. | 424/49 |
| 4,647,600 | 3/1987 | Kawahara et al. | 523/116 |
| 4,652,593 | 3/1987 | Kawahara et al. | 523/116 |
| 4,678,436 | 7/1987 | Kondo et al. | 433/228.1 |
| 4,775,592 | 10/1988 | Akahane et al. | 428/406 |
| 4,900,697 | 2/1990 | Akahane et al. | 501/57 |
| 5,063,257 | * 11/1991 | Akahane et al. | 523/116 |
| 5,844,019 | * 12/1998 | Kato | 523/115 |
| 5,871,360 | * 2/1999 | Kato | 523/116 |
| 5,962,550 | 10/1999 | Akahane et al. | 523/116 |

* cited by examiner

Primary Examiner—C. Melissa Koslow
(74) Attorney, Agent, or Firm—Oblon, Spivak, McClelland, Maier & Neustadt, P.C.

(57) ABSTRACT

A dental adhesive set is disclosed, comprising (I) a tooth surface conditioning agent and (II) a bonding material, wherein the tooth surface conditioning agent (I) is an acid aqueous solution, and the bonding material (II) comprises a mixture of: (a) a fluoroalumino silicate glass powder, (b) one or two or more unsaturated organic compounds selected from polymerizable unsaturated organic compounds having at least one $CH_2=CR_1-COO-$, wherein $R_1$ is H or $CH_3$, and not having an acid group; (c) an acid; (d) water; and (e) a photopolymerization catalyst. According to the dental adhesive set of the present invention, the dental restoration and the dentin can be firmly and surely adhered to each other in a clinically simple operation, and by imparting properties for continuously releasing a fluoride ion not only the dentinal restoration but also the reinforcement of tooth structure and the inhibition of secondary caries can be expected.

4 Claims, No Drawings

DENTAL ADHESIVE SET

BACKGROUND OF THE INVENTION

1. Field of the Invention

The present invention relates to a dental adhesive set comprising a tooth surface conditioning agent and a bonding material, which is used for adhering a dental composite resin to a tooth structure. More particularly, it relates to a dental adhesive set for continuously releasing a fluoride ion which is considered to be effective for reinforcing a tooth structure when a dental restorative material such as a dental composite resin is adhered to an enamel/dentin.

2. Description of the Related Art

A dental composite resin as a dental restorative material is superior in esthetics and has superior in mechanical properties and handling. For these reasons, the dental composite resin is now widely used as a dental restorative material. However, the composite resin itself has no adhesive properties to a tooth structure. For this reason, in order that the dental composite resin is adhered to a tooth structure, it is considered to be necessary to use an exclusive adhesive having strong adhesive properties, which is simple in handling and safe and reliable. Dental adhesives which have hitherto been used are composed mainly of an unsaturated organic compound and a polymerization catalyst for polymerizing it for curing and optionally, an adhesive monomer, etc. The dental adhesive is used upon application when the dental composite resin is filled. However, since when only the dental adhesive is used, a sufficient adhesive strength is not obtained, it is necessary to subject a cavity to tooth surface conditioning or priming in advance.

In a representative adhesion handling method are employed a series of handlings in which tooth surface conditioning of a tooth structure with an acid solution such as phosphoric acid or citric acid, water washing, drying, priming, drying, application of a bonding material, polymerization, and filling of a composite resin are carried out in this order. Also, there has been known a method in which tooth surface conditioning using a self-etching primer composed of, as a cavity conditioner, an adhesive monomer containing a hydrophilic group such as a phosphoric acid group or a carboxyl group, water, a solvent, a polymerization catalyst, etc., drying, application of a bonding material, polymerization, and filling of a composite resin are carried out in this order.

In recent years, in the preventive dentistry field, expecting a reinforcement of tooth structure and inhibition of a secondary caries by a fluoride ion are used many dental products containing fluoride, such as a fluoride application agent, a fluoride-containing toothpaste, and a fluoride-containing pit and fissure sealant. In addition, in dental restorative materials, a glass ionomer cement is drawing the attention as a material having properties for continuously releasing a fluoride ion and has widely been used for various applications such as a filling material, a luting material, a lining material, a pit and fissure sealant, and an adhesive. However, the glass ionomer is required to mix a fluoride-containing fluoroalumino silicate glass powder and a carboxylic acid aqueous solution at the time of use and therefore, involves a defect that the handling is complicated.

On the other hand, though the dental composite resin which is clinically used frequently every day because the handling as a restorative is simple and is superior in mechanical properties, esthetics, and handling, it does not have properties for releasing a fluoride ion. Further, the dental adhesive which is used together with the restorative composite resin does not have properties for releasing a fluoride ion. Accordingly, it can not be said that the restoration by the composite resin and the adhesive expects the reinforcement of tooth structure or inhibition of secondary caries.

In recent years, products in which a fluoride is contained in a composite resin or a dentinal adhesive are being developed. However, since the fluoride compound used in these products is soluble in water, when it comes into contact with a saliva in the oral cavity, a fluoride ion is released from the material within a short period of time so that an effective reinforcement of tooth structure can not be expected. Also, this causes lowering of the mechanical properties of the material itself.

SUMMARY OF THE INVENTION

The present inventors have paid an attention to a point that the composite resin or the dental adhesive used for the dental restoration does not have properties for continuously releasing a fluoride ion which can be expected to have a reinforcement of tooth structure function or inhibition of a secondary caries as well as to a point that the glass ionomer cement having properties for continuously releasing a fluoride ion is required to be kneaded at the time of use and hence, is difficult in operation. Thus, an object of the present invention is to provide a dental adhesive set comprising a tooth surface conditioning agent and a bonding material which is of one-pack type and does not require mixing, which can firmly and surely adhere a dental restoration to a tooth structure by a clinically simple manipulation and can achieve dental restoration, reinforcement of tooth structure and have inhibition of secondary dental caries by imparting properties for continuously releasing a fluoride ion to the bonding material.

In order to achieve the above-described object of the invention, the present inventors have made extensive and intensive investigations. As a result, we have successfully developed a one-pack type photopolymerizable bonding material having properties for continuously releasing a fluoride ion by containing a fluoroalumino silicate glass powder, an acid, and water into a polymerizable unsaturated organic compound having at least one $CH_2=CR_1-COO-$, wherein $R_1$ is H or $CH_3$, and not having an acid group, thereby previously undergoing an acid-base reaction among the fluoroalumino silicate glass powder, the acid, and water to obtain a one-pack type paste or suspension; and further compounding a photopolymerization catalyst thereinto.

Moreover, it has been found that when used together with an acid-containing tooth surface conditioning agent which is used for usual dental adhesives, this one-pack type mixing-free bonding material can be expected to have superior adhesive durability and reinforcement of tooth structure by a fluoride ion continuously released from the adhered portion, leading to completion of a dental adhesive set according to the present invention, which comprises a tooth surface conditioning agent and a bonding material.

This dental adhesive set according to the present invention can ensure a proper thickness of a coating film in the cavity because the bonding material has a proper viscosity. Thus, a space between the tooth structure and the dental composite resin can be surely sealed, thereby obtaining superior fitness without generating a gap therebetween.

The dental adhesive set according to the present invention comprises (I) a tooth surface conditioning agent and (II) a bonding material, wherein the tooth surface conditioning agent (I) is an acid aqueous solution, and the bonding material (II) comprises a mixture of:
(a) a fluoroalumino silicate glass powder,
(b) one or two or more unsaturated organic compounds selected from polymerizable unsaturated organic compounds having at least one $CH_2=CR_1-COO-$, wherein $R_1$ is H or $CH_3$, and not having an acid group;
(c) an acid;
(d) water; and
(e) a photopolymerization catalyst.

DETAILED DESCRIPTION OF THE INVENTION

Each of the tooth surface conditioning agent and the bonding material constituting the dental adhesive set according to the present invention is hereunder described.

In order to draw out the performance of the bonding material effectively, the tooth surface conditioning agent (I) has such a function that it is applied on a tooth surface to be adhered prior to the application of the bonding material, thereby modifying the tooth structure. As the tooth surface conditioning agent (I), usually tooth surface conditioning agents comprised of an aqueous solution mainly containing an acid such as phosphoric acid, citric acid, or maleic acid can be used. Besides, are also usable tooth surface conditioning agents containing an acid, which are usually used as a dental adhesive, such as tooth surface conditioning agents usually called as a self-etching primer, comprising a monomer containing a hydrophilic group such as phosphoric acid group or a carboxyl group, water, a solvent, a polymerization catalyst, and the like.

The bonding material (II) directly influences the adhesion and is a most characteristic part in the dental adhesive set according to the present invention.

The fluoroalumino silicate glass powder (a) contained in the bonding material (II) is a fluoroalumino silicate glass powder containing $Al^{3+}$, $Si^{4+}$, $F^-$ and $O^{2-}$ as the major components and additionally containing $Sr^{2+}$ and/or $Ca^{2+}$ and suitably has a mean particle size of 0.02 μm to 10 μm. Of those are preferred ones having a mean particle size of 0.02 μm to 5 μm. When a fine powder having a mean particle size of less than 0.02 μm is used, the reaction with the acid proceeds so fast that the reaction product between the fluoroalumino silicate glass powder and the acid/water is coagulated in the bonding material, whereby a bonding material of good handling is no longer available. On the other hand, when the mean particle size of the fluoroalumino silicate glass powder exceeds 10 μm, since the reaction product between the fluoroalumino silicate glass powder and the acid/water has a large particle size, a sedimentation phenomenon is generated in the bonding material with a lapse of time, whereby the manipulation and the properties for releasing a fluoride ion become worse. The fluoroalumino silicate glass powder is preferably contained in an amount ranging 5% to 70% by weight in the bonding material component. When the amount of the fluoroalumino silicate glass is less than 5% by weight, the properties for continuously releasing a fluoride ion are lowered, and the viscosity is too low, thereby making it difficult to obtain a suitable thickness of the coating film. On the other hand, when it exceeds 70% by weight, the viscosity of the bonding material is too high, whereby the handling during the application is liable to become worse, and the adhesive properties tend to be lowered. As the fluoroalumino silicate glass powder (a) contained in the bonding material (II), those obtained by the usual silane processing can be used.

The component (b), one or two or more unsaturated organic compounds selected from polymerizable unsaturated organic compounds having at least one $CH_2=CR_1-COO-$, wherein $R_1$ is H or $CH_3$, and not having an acid group, which is contained in the bonding material (II), refers to a polymerizable unsaturated organic compound having an acryloyl group or a methacryloyl group, such as acrylic or methacrylic esters, and is a component having a function to enhance the permeability into a decalcified tooth structure and having a function to enhance the strength of a dental adhesive having properties for continuously releasing a fluoride ion upon polymerization by the function of the component (e), polymerization catalyst, as described hereunder in detail. Examples of the unsaturated organic compounds which can be used in the present invention include methyl methacrylate, ethyl methacrylate, isopropyl methacrylate, 2-hydroxyethyl methacrylate, 3-hydroxypropyl methacrylate, 2-hydroxy-1,3-dimethacryloxypropane, n-butyl methacrylate, isobutyl methacrylate, hydroxypropyl methacrylate, tetrahydrofurfuryl methacrylate, glycidyl methacrylate, 2-methoxyethyl methacrylate, 2-ethylhexyl methacrylate, 2,2-bis(methacryloxyphenyl)propane, 2,2-bis[4-(2-hydroxy-3-methacryloxypropoxy)phenyl]propane, 2,2-bis(4-methacryloxy-diethoxyphenyl)propane, 2,2-bis(4-methacryloxypolyethoxyphenyl)propane, ethylene glycol dimethacrylate, diethylene glycol dimethacrylate, triethylene glycol dimethacrylate, butylene glycol dimethacrylate, neopentyl glycol dimethacrylate, 1,3-butanediol dimethacrylate, 1,4-butanediol dimethacrylate, 1,6-hexanediol dimethacrylate, trimethylolpropane trimethacrylate, trimethylolethane trimethacrylate, pentaerythritol trimethacrylate, trimethylolmethane trimethacrylate, pentaerythritol tetramethacrylate, and acrylates corresponding thereto. Also, as the methacrylate or acrylate having a urethane bond in the molecule, are usable di-2-methacryloxyethyl-2,2,4-trimethylhexamethylene dicarbamate and an acrylate corresponding thereto.

The component (b), one or two or more unsaturated organic compounds selected from polymerizable unsaturated organic compounds having at least one $CH_2=CR_1-COO-$, wherein $R_1$ is H or $CH_3$, and not having an acid group, is preferably contained in an amount of 25% to 95% by weight in the bonding material (II). When the amount of the component (b) is less than 25% by weight, the viscosity of the bonding material (II) is too high, whereby the handling during the application and the adhesive properties are lowered. On the other hand, when it exceeds 95% by weight, the properties for continuously releasing a fluoride ion are lowered. Further, the viscosity is too low, thereby making to difficult to obtain a suitable coating film thickness.

The acid (c) which is contained in the boding material is an inorganic acid and/or an organic acid. Examples of such acids include phosphoric acid, hydrochloric acid, sulfuric acid, nitric acid, citric acid, succinic acid, boric acid, fumaric acid, tartaric acid, malic acid, maleic acid, ethylenediaminetetraacetic acid, tricarballylic acid, levulinic acid, acidic amino acid, polymers of an α,β-unsaturated carboxylic acid, and methacrylates or acrylates having an acid group. These acids can be used singly or in admixture of two or more thereof. Of those, are preferred phosphoric acid, hydrochloric acid, citric acid, tartaric acid, malic acid, maleic acid, tricarballylic acid, levulinic acid, pyroglutamic acid, polymers of an α,β-unsaturated carboxylic acid having a weight average molecular weight of from 5,000 to 40,000, and methacrylates or acrylates having an acid group.

The polymers of an α,β-unsaturated carboxylic acid having a weight average molecular weight of 5,000 to 40,000 referred to herein mean polymers of an α,β-unsaturated monocarboxylic acid or of an α,β-unsaturated dicarboxylic acid. Examples thereof include homopolymers or copolymers of acrylic acid, methacrylic acid, 2-chloroacrylic acid, aconitic acid, mesaconic acid, maleic acid, itaconic acid, fumaric acid, glutaconic acid, citraconic acid, etc. These copolymers may be a copolymer between α,β-unsaturated carboxylic acids, or a copolymer of an α,β-unsaturated carboxylic acid and a copolymerizable component. In the latter case, it is preferable that the proportion of the α,β-unsaturated carboxylic acid is 50% or more. Examples of the copolymerizable component include acrylamide, acrylonitrile, methacrylic esters, acrylic acid salts, vinyl chloride, allyl chloride, and vinyl acetate. Of these polymers of an α,β-unsaturated carboxylic acid is preferable a homopolymer or copolymer of acrylic acid or maleic acid. With respect to the polymers of an α,β-unsaturated carboxylic acid, when the weight average molecular weight is less than 5,000, the strength of the reaction product is low, thereby producing problems in physical properties, etc. On the other hand, when it exceeds 40,000, the viscosity is too high, so that such is not suitable for the use.

The methacrylate or acrylate having an acid group as referred to herein means a methacrylate or acrylate monomer having an acid group such as a phosphoric acid group, a carboxyl group, and a sulfonic acid group. Examples thereof include 2-(meth)acryloyloxyethyl dihydrogenphosphate, bis[2-(meth)acryloyloxyethyl] hydrogenphosphate, 2-(meth)acryloyloxyethylphenyl acid phosphate, 6-(meth)acryloyloxybutyl acid phosphate, 8-(meth)acryloyloxydecyl acid phosphate, 10-(meth) acryloyloxydecyl dihydrogenphosphate, (meth)acrylic acid, 4-(meth)acryloxyethyl trimellitic acid and an anhydride thereof, 6-(meth)acryloyloxyethyl naphthalene-1,2,6-tricarboxylic acid and an anhydride thereof, 1,4-di(meth) acryloyloxyethyl pyromellitic acid, 2-(meth) acryloyloxyethyl succinic acid, 2-(meth)acryloyloxyethyl maleic acid, 2-(meth)acryloyloxyethyl phthalic acid, 2-(meth)acryloyloxyethyl hexahydrophthalic acid, 11-(meth)acryloyloxy-1,1-undecanedicarboxylic acid, N-(meth)acryloyl-p-aminobenzoic acid, N-(meth)acryloyl-o-aminobenzoic acid, N-(meth)acryloyl-5-aminosalicylic acid, 2-sulfoethyl (meth)acrylate, and 2-(meth)acrylamido-2-methylpropanesulfonic acid. These methacrylate or acrylate monomers having an acid group such as a phosphoric acid group, a carboxyl group, and a sulfonic acid group can be used singly or in admixture of two or more thereof. Of those, are particularly preferable bis[2-(meth) acryloyloxyethyl] hydrogenphosphate, 2-(meth) acryloyloxyethylphenyl acid phosphate, 10-(meth) acryloyloxydecyl dihydrogenphosphate, 4-(meth) acryloyloxyethyl trimellitic acid and an anhydride thereof, 6-(meth)acryloyloxyethyl naphthalene-1,2,6-tricarboxylic acid and an anhydride thereof, 1,4-di(meth)acryloyloxyethyl pyromellitic acid, and 2-(meth)acrylamido-2-methylpropanesulfonic acid.

A suitable amount of the acid (c) contained in the bonding material (II) is from 1% to 15% by weight in the bonding material (II). When the amount of the acid (c) is less than 1% by weight, the properties for continuously releasing a fluoride ion are lowered, whereas when it exceeds 15% by weight, the mechanical strength and storage stability of the bonding material become worse.

As the water (d) contained in the bonding material (II), are usable ones containing no impurities. Examples thereof include distilled water, purified water, ion-exchanged water, and deionized water. A suitable amount of the water (d) is from 1% to 15% by weight in the bonding material (II). When the amount of the water (d) is less than 1% by weight, the reactivity between the acid (c) and the fluoroalumino silicate glass powder (a) is insufficient so that the properties for continuously releasing a fluoride ion and the storage stability are lowered. On the other hand, when it exceeds 15% by weight, the mechanical strength of the bonding material (II) is lowered.

As the photopolymerization catalyst (e) contained in the bonding material (II), is usable a combination of a sensitizer with a reducing agent.

Examples of the sensitizer which can be used in the present invention include camphorquinone, benzil, diacetyl, benzyl dimethyl ketal, benzyl diethyl ketal, benzyl di(2-methoxyethyl) ketal, 4,4'-dimethylbenzyl-dimethyl ketal, anthraquinone, 1-chloroanthraquinone, 2-chloroanthraquinone, 1,2-benzanthraquinone, 1-hydroxyanthraquinone, 1-methylanthraquinone, 2-ethylanthraquinone, 1-bromoanthraquinone, thioxanthone, 2-isopropylthioxanthone, 2-nitrothioxanthone, 2-methylthioxanthone, 2,4-dimethylthioxanthone, 2,4-diethylthioxanthone, 2,4-diisopropylthioxanthone, 2-chloro-7-trifluoromethyl-thioxanthone, thioxanthone-10,10-dioxide, thioxanthone-10-oxide, benzoinmethyl ether, benzoinethyl ether, benzoinisopropyl ether, benzoinisobutyl ether, benzophenone, bis(4-dimethylaminophenyl) ketone, 4,4'-bisdiethylamino-benzophenone, and azido containing compounds. These sensitizers can be used singly or in admixture.

As the reducing agent, are usable various reducing agents including tertiary amines. Preferred examples of the tertiary amines which can be used in the present invention include N,N-dimethyl-p-toluidine, N,N-dimethylaminoethyl methacrylate, triethanolamine, methyl 4-dimethylaminobenzoate, ethyl 4-dimethylaminobenzoate, and isoamyl 4-dimethylaminobenzoate. These tertiary amines can be used singly or in admixture. A suitable amount of the photopolymerization catalyst (e) is from 0.1% to 5% by weight. When the amount of the photopolymerization catalyst (e) is less than 0.1% by weight, a polymerization will not be fully secured. On the other hand, even when it exceeds 5% by weight, the effects are no longer improved.

In the bonding material according to the present invention, if desired, in order to control the storage stability and the handling, a polymerization inhibitor, an ultraviolet light absorber, a coloring agent, a filler, and the like may be properly compounded.

The dental adhesive set according to the present invention is specifically described with reference to the following Examples, but it is to be not construed that the invention is limited thereto.

[Preparation of Fluoroalumino Silicate Glass Powder]

The fluoroalumino silicate glass powders used in the respective Examples and Comparative Examples were prepared in the following manners.

Fluoroalumino Silicate Glass Powder (1):

Twenty-three grams of aluminum oxide, 30 g of silicic anhydride, 30 g of strontium fluoride, 5 g of aluminum phosphate, and 12 g of aluminum fluoride were mixed, and the mixture was kept in a high-temperature electric furnace at 1,300° C. for 5 hours, thereby melting a glass. After melting, the glass was cooled, pulverized in a ball mill for 10 hours, and passed through a 200-mesh (ASTM) sieve to prepare a fluoroalumino silicate glass powder. To 100 parts by weight of this glass powder was added 30 parts by weight of an ethanol solution containing 15% of 3-methacryloxypropyl trimethoxysilane, and mixed in a mortar. The resulting mixture was subjected by drying at 120° C. for 2 hours using a steam dryer. The thus-obtained glass powder had a specific gravity of 3.0 and a mean particle size of 2.2 µm.

Fluoroalumino Silicate Glass Powder (2):

Twenty-three grams of aluminum oxide, 41 g of silicic anhydride, 10 g of calcium fluoride, 13 g of calcium phosphate, and 13 g of aluminum fluoride were mixed, and the mixture was kept in a high-temperature electric furnace at 1,100° C. for 5 hours, thereby melting a glass. After melting, the glass was cooled, pulverized in a ball mill for 10 hours, and passed through a 200-mesh (ASTM) sieve to prepare a fluoroalumino silicate glass powder. To 100 parts by weight of this glass powder was added 30 parts by weight of an ethyl alcohol solution containing 10% of vinyl triethoxysilane, and mixed in a mortar. The resulting mixture was subjected by drying at 110° C. for 2 hours using a steam dryer. The thus-obtained glass powder had a specific gravity of 3.3 and a mean particle size of 2.3 µm.

EXAMPLE 1

[Tooth Surface Conditioning Agent]

A tooth surface conditioning agent was prepared by mixing and dissolving 15% by weight of citric acid, 2% by weight of ferric chloride, and 83% by weight of distilled water.

[Bonding Material]

25% by weight of 2-hydroxyethyl methacrylate, 22.5% by weight of triethylene glycol dimethacrylate, 10% by weight of di-2-methacryloxyethyl-2,2,4-trimethylhexa-methylene dicarbamate, 5% by weight of distilled water, 5% by weight of citric acid, and 30% by weight of the fluoroalumino silicate glass powder (1) were mixed in an automatic mortar for 5 hours to obtain a paste. The paste was further added and mixed with 1.0% by weight of camphorquinone and 1.5% by weight N,N-dimethylaminoethyl methacrylate to prepare a bonding material.

Using the thus prepared tooth surface conditioning agent and bonding material, the adhesive strength and the released amount of fluoride ion were measured in the manners as described below. The compounding composition, the compounding amount, and the results are shown in Table 1.

[Measurement of Adhesive Strength]

1. A surface of fresh bovine anterior teeth was polished with a waterproof paper #600 while pouring water, and 5 enamels and 5 dentins were exposed to obtain surfaces to be adhered.

2. The polished dentin surface or enamel surface was masked with a fluorocarbon resin-made tape having an opening with a diameter of 3.0 mm to define a surface to be adhered. Onto the thus defined surface to be adhered was applied the tooth surface conditioning agent and kept for 20 seconds. Thereafter, The resulting surface was cleaned with water and dried by air under a low pressure. However, in case where the self-etching type tooth surface conditioning agent was used, the water cleaning was omitted, and only the drying by air under a low pressure was carried out. Subsequently, the bonding material was applied thereonto and irradiated with a light by means of a dental visible ray irradiator (a trade name: GC New Light VL-II, manufactured by GC Corporation) for 20 seconds.

3. On the surface to be adhered was built up a photopolymerization type composite resin (a trade name: Estio LC, manufactured by GC Corporation) in a 2.0 mm-thick silicone rubber mold having an opening with an inside diameter of 5.0 mm, followed by irradiation with a light for 40 seconds using a visible light irradiator (a trade name: GC New Light VL-II, manufactured by GC Corporation), thereby curing the resin.

4. The test specimen was immersed in water at 37° C. for one day, and an acrylic resin-made rod for adhesion test was fixed in the upper part of the specimen. Thereafter, each of the specimens was subjected to a tensile adhesion test by means of a universal tester (a product name: Autograph, manufactured by Shimadzu Corporation) at a cross-head speed of 1.0 mm/min. From the results of the measurement of adhesion to the enamel and the dentin, an average value of the respective five specimens was obtained and taken to be an adhesive strength.

[Measurement of Amount of Fluoride Ion Release]

1. The bonding material was filled in an acrylic resin-made mold having an opening with a diameter of 6 mm and a thickness of 1 mm.

2. The specimen was irradiated with a light for 20 seconds using a visible light irradiator (a trade name: GC New Light LV-II, manufactured by GC Corporation).

3. The specimen was kept in a chamber at 37° C. and at a humidity of 100% for one hour and then moved into a glass bottle, into which was charged 8 ml of distilled water for immersing.

4. Twenty-four hours after the immersing, the specimen was taken out from the water, and while cleaning the surface of the specimen with 2 ml of distilled water, the total amount of the test solution was adjusted to 10 ml. To this test solution was added 1 ml of a total ionic strength regulator, and the concentration of fluoride ion in the test solution was measured using fluoride ion electrodes to obtain a released amount of fluoride ion after 24 hours.

5. The specimen was newly immersed in 8 ml of distilled water and kept in a chamber at 37° C.

6. The distilled water was exchanged every 24 hours, and the released amount of fluoride ion was measured using fluoride ion electrodes for one month in the same manner as in the measurement of the released amount of fluoride ion after 24 hours as described above. The released amount of fluoride ion after one month was summarized as an integrated released amount. The released amount of fluoride ion shown in Table 1 is an average value of the three specimens in terms of mg/ml.

EXAMPLES 2 to 15

Tooth surface conditioning agent and bonding materials each having the composition and the compounding amount as shown in Table 1 were prepared in the same manner as in Example 1 and subjected to the same tests as in Example 1. The results are shown in Table 1.

TABLE 1

| | Tooth surface conditioning agent | | | Bonding material | | | Adhesive strength [MPa] ( ): Standard deviation Enamel | Adhesive strength [MPa] ( ): Standard deviation Dentin | Released amount of fluoride ion [mg/ml] After 24 hours | Released amount of fluoride ion [mg/ml] After one month |
|---|---|---|---|---|---|---|---|---|---|---|
| Example 1 | Citric acid | 15 | wt % | 2-Hydroxyethyl methacrylate | 25 | wt % | 15.3 (3.1) | 13.8 (2.2) | 19.6 | 27.4 |
| | Distilled water | 83 | wt % | Triethylene glycol dimethacrylate | 22.5 | wt % | | | | |
| | Ferric chloride | 2 | wt % | Di-2-methacryloxyethyl-2,2,4-trimethylhexamethylene dicarbamate | 10 | wt % | | | | |
| | | | | Distilled water | 5 | wt % | | | | |
| | | | | Citric acid | 5 | wt % | | | | |
| | | | | Fluoroalumino silicate glass powder (1) | 30 | wt % | | | | |
| | | | | Camphorquinone | 1 | wt % | | | | |
| | | | | N,N-Dimethylaminoethyl methacrylate | 1.5 | wt % | | | | |
| Example 2 | Polyacrylic acid | 20 | wt % | 2-Hydroxyethyl methacrylate | 17 | wt % | 14.4 (2.8) | 12.9 (2.4) | 17.6 | 24.6 |
| | Aluminum chloride | 2 | wt % | Triethylene glycol dimethacrylate | 20 | wt % | | | | |
| | Distilled water | 78 | wt % | Distilled water | 5 | wt % | | | | |
| | | | | Polyacrylic acid having an average molecular weight of 18,000 | 5 | wt % | | | | |
| | | | | Fluoroalumino silicate glass powder (1) | 50 | wt % | | | | |
| | | | | Camphorquinone | 1.5 | wt % | | | | |
| | | | | Methyl 4-dimethylaminobenzoate | 1.5 | wt % | | | | |
| Example 3 | Phosphoric acid | 10 | wt % | 2-Hydroxyethyl methacrylate | 30.5 | wt % | 15.5 (2.7) | 13.2 (3.1) | 21.1 | 27.9 |
| | Ferric chloride | 0.5 | wt % | Triethylene glycol dimethacrylate | 10 | wt % | | | | |
| | Distilled water | 89.5 | wt % | 2,2-Bis[4-(2-hydroxy-3-methacryloxy-propoxy)phenyl]propane | 5 | wt % | | | | |
| | | | | Distilled water | 12 | wt % | | | | |
| | | | | Polyacrylic acid having an average molecular weight of 8,000 | 10 | wt % | | | | |
| | | | | Fluoroalumino silicate glass powder (2) | 28 | wt % | | | | |
| | | | | Camphorquinone | 1.5 | wt % | | | | |
| | | | | Isoamyl 4-dimethylaminobenzoate | 3 | wt % | | | | |
| Example 4 | 2-Methacryloyloxyethyl dihydrogenphosphate | 20 | wt % | 2-Hydroxyethyl methacrylate | 15.5 | wt % | 18.2 (3.0) | 16.8 (2.9) | 10.5 | 15.2 |
| | | | | 2-Hydroxy-1,3-dimethacryloxypropane | 25 | wt % | | | | |
| | 2-Hydroxyethyl methacrylate | 3 | wt % | Di-2-methacryloxyethyl-2,2,4-trimethylhexamethylene dicarbamate | 18 | wt % | | | | |
| | Distilled water | 30 | wt % | Distilled water | 1 | wt % | | | | |
| | Ethyl alcohol | 46 | wt % | 4-Methacryloxyethyl trimellitic acid | 4 | wt % | | | | |
| | Camphorquinone | 1 | wt % | Fluoroalumino silicate glass powder (2) | 35 | wt % | | | | |
| | | | | Camphorquinone | 0.5 | wt % | | | | |
| | | | | Isoamyl 4-dimethylaminobenzoate | 1 | wt % | | | | |
| Example 5 | 4-Methacryloxyethyl trimellitic acid | 10 | wt % | 2-Hydroxyethyl methacrylate | 41 | wt % | 16.8 (3.4) | 18.8 (2.9) | 5.8 | 7.7 |
| | 1,4-Dimethacryloyloxyethyl pyromellitic acid | 7 | wt % | Triethylene glycol dimethacrylate | 30 | wt % | | | | |
| | | | | Di-2-methacryloxyethyl-2,2,4-trimethylhexamethylene dicarbamate | 20 | wt % | | | | |
| | Distilled water | 35 | wt % | Distilled water | 1 | wt % | | | | |
| | Acetone | 47.5 | wt % | Tartaric acid | 1 | wt % | | | | |
| | Camphorquinone | 0.5 | wt % | Fluoroalumino silicate glass powder (1) | 5 | wt % | | | | |
| | | | | Ethyl 4-dimethylaminobenzoate | 1 | wt % | | | | |
| | | | | Camphorquinone | 1 | wt % | | | | |
| Example 6 | Citric acid | 15 | wt % | 2-Hydroxyethyl methacrylate | 50 | wt % | 13.8 (3.2) | 13.5 (3.3) | 15.2 | 22.5 |
| | Distilled water | 83 | wt % | Neopentyl glycol dimethacrylate | 4 | wt % | | | | |
| | Ferric chloride | 2 | wt % | Di-2-methacryloxyethyl-2,2,4-trimethylhexamethylene dicarbamate | 20 | wt % | | | | |
| | | | | Distilled water | 10 | wt % | | | | |
| | | | | Acrylic acid/maleic acid copolymer having an average molecular weight of 24,000 | 3 | wt % | | | | |
| | | | | Fluoroalumino silicate glass powder (1) | 10 | wt % | | | | |
| | | | | Camphorquinone | 1 | wt % | | | | |
| | | | | N,N-Dimethylaminoethyl methacrylate | 2 | wt % | | | | |
| Example 7 | 2-Methacryloyloxyethyl dihydrogenphosphate | 20 | wt % | 2-Hydroxyethyl methacrylate | 20 | wt % | 15.6 (3.3) | 16.3 (2.9) | 14.8 | 21.2 |
| | | | | Glycidyl methacrylate | 5 | wt % | | | | |
| | | | | Di-2-methacryloxyethyl-2,2,4-trimethylhexamethylene dicarbamate | 3 | wt % | | | | |
| | 2-Hydroxyethyl methacrylate | 3 | wt % | Distilled water | 2 | wt % | | | | |
| | Distilled water | 30 | wt % | Levulinic acid | 2 | wt % | | | | |
| | Ethyl alcohol | 46 | wt % | Fluoroalumino silicate glass powder (1) | 67.7 | wt % | | | | |
| | Camphorquinone | 1 | wt % | Camphorquinone | 0.1 | wt % | | | | |
| | | | | Ethyl 4-dimethylaminobenzoate | 0.2 | wt % | | | | |
| Example 8 | 2-Methacryloyloxyethyl-dihydrogenphosphate | 20 | wt % | 2-Hydroxyethyl methacrylate | 25 | wt % | 17.4 (3.6) | 17.9 (2.8) | 15.6 | 21.4 |
| | | | | Triethylene glycol dimethacrylate | 22.5 | wt % | | | | |
| | | | | Di-2-methacryloxyethyl-2,2,4-trimethylhexamethylene dicarbamate | 10 | wt % | | | | |
| | 2-Hydroxyethyl methacrylate | 3 | wt % | Distilled water | 5 | wt % | | | | |

TABLE 1-continued

| Example | Tooth surface conditioning agent | | Bonding material | | Adhesive strength [MPa] ( ): Standard deviation Enamel | Dentin | Released amount of fluoride ion [mg/ml] After 24 hours | After one month |
|---|---|---|---|---|---|---|---|---|
| | Distilled water | 30 wt % | Pyroglutamic acid | 3 wt % | | | | |
| | Ethyl alcohol | 46 wt % | Fluoroalumino silicate glass powder (1) | 32 wt % | | | | |
| | Camphorquinone | 1 wt % | Camphorquinone | 1 wt % | | | | |
| | | | N,N-Dimethylaminoethyl methacrylate | 1.5 wt % | | | | |
| Example 9 | 4-Methacryloxyethyl trimellitic anhydride | 14 wt % | 2-Hydroxyethyl methacrylate | 35 wt % | 16.8 (2.9) | 17.3 (2.9) | 11.8 | 16.5 |
| | 2-Hydroxy-1,3-dimethacryoyloxy-propane | 1 wt % | Triethylene glycol dimethacrylate | 27.5 wt % | | | | |
| | | | Di-2 methacryloxyethyl-2,2,4-trimethylhexamethylene dicarbamate | 10 wt % | | | | |
| | Distilled water | 30 wt % | Distilled water | 3 wt % | | | | |
| | Acetone | 30 wt % | 2-Methacryloyloxyethyl dihydrogen-phosphate | 2 wt % | | | | |
| | Ethyl alcohol | 24.8 wt % | Fluoroalumino silicate glass powder (1) | 20 wt % | | | | |
| | Camphorquinone | 0.2 wt % | Camphorquinone | 0.5 wt % | | | | |
| | | | Isoamyl 4-dimethylaminobenzoate | 2.0 wt % | | | | |
| Example 10 | Citric acid | 15 wt % | 2-Hydroxyethyl methacrylate | 42 wt % | 13.5 (1.9) | 132.8 (2.5) | 4.1 | 5.3 |
| | Distilled water | 83 wt % | Triethylene glycol dimethacrylate | 8 wt % | | | | |
| | Ferric chloride | 2 wt % | Di-2-methacryloxyethyl-2,2,4-trimethylhexamethylene dicarbamate | 7 wt % | | | | |
| | | | Distilled water | 10 wt % | | | | |
| | | | Phosphoric acid | 1 wt % | | | | |
| | | | Fluoroalumino silicate glass powder (1) | 30 wt % | | | | |
| | | | Camphorquinone | 1 wt % | | | | |
| | | | Ethyl 4-dimethylaminobenzoate | 1 wt % | | | | |
| Example 11 | Citric acid | 15 wt % | 2-Hydroxyethyl methacrylate | 42 wt % | 14.2 (2.2) | 13.7 (2.6) | 4.3 | 6.3 |
| | Distilled water | 83 wt % | Triethylene glycol dimethacrylate | 8 wt % | | | | |
| | Ferric chloride | 2 wt % | Di-2-methacryloxyethyl-2,2,4-trimethylhexamethylene dicarbamate | 7 wt % | | | | |
| | | | Distilled water | 10 wt % | | | | |
| | | | Hydrochloric acid | 1 wt % | | | | |
| | | | Fluoroalumino silicate glass powder (1) | 30 wt % | | | | |
| | | | Camphorquinone | 1 wt % | | | | |
| | | | Ethyl 4-dimethylaminobenzoate | 1 wt % | | | | |
| Example 12 | 2-Methacryloyloxyethyl dihydrogen-phosphate | 29 wt % | 2-Hydroxyethyl methacrylate | 25 wt % | 15.5 (3.2) | 15.7 (2.9) | 12.6 | 16.8 |
| | 2-Hydroxyethyl methacrylate | 3 wt % | Triethylene glycol dimethacrylate | 22.5 wt % | | | | |
| | | | Di-2-methacryloxyethyl-2,2,4-trimethylhexamethylene dicarbamate | 10 wt % | | | | |
| | | | Distilled water | 5 wt % | | | | |
| | Distilled water | 30 wt % | Malic acid | 3 wt % | | | | |
| | Ethyl alcohol | 46 wt % | Fluoroalumino silicate glass powder (1) | 32 wt % | | | | |
| | Camphorquinone | 1 wt % | Camphorquinone | 1 wt % | | | | |
| | | | N,N-Dimethylaminoethyl methacrylate | 1.5 wt % | | | | |
| Example 13 | 4-Methacryloxyethyl trimellitic anhydride | 14 wt % | 2-Hydroxyethyl methacrylate | 25 wt % | 15.1 (3.3) | 15.0 (3.2) | 11.0 | 15.6 |
| | 2-Hydroxy-1,3-dimethacryloxy-propane | 1 wt % | Triethylene glycol dimethacrylate | 22.5 wt % | | | | |
| | | | Di-2-methacryloxyethyl-2,2,4-trimethylhexamethylene dicarbamate | 10 wt % | | | | |
| | Distilled water | 30 wt % | Distilled water | 5 wt % | | | | |
| | Acetone | 30 wt % | Maleic acid | 3 wt % | | | | |
| | Ethyl alcohol | 24.8 wt % | Fluoroalumino silicate glass powder (1) | 32 wt % | | | | |
| | Camphorquinone | 0.2 wt % | N,N-Dimethylaminoethyl methacrylate | 1.5 wt % | | | | |
| Example 14 | 4-Methacryloxyethyl trimellitic anhydride | 14 wt % | 2-Hydroxyethyl methacrylate | 25 wt % | 16.0 (3.3) | 16.4 (2.9) | 12.4 | 16.6 |
| | 2-Hydroxy-1,3-dimethacryloxy-propane | 1 wt % | Triethylene glycol dimethacrylate | 22.5 wt % | | | | |
| | | | Di-2-methacryloxyethyl-2,2,4-trimethylhexamethylene dicarbamate | 10 wt % | | | | |
| | Distilled water | 30 wt % | Distilled water | 5 wt % | | | | |
| | Acetone | 30 wt % | Tricarballylic acid | 3 wt % | | | | |
| | Ethyl alcohol | 24.8 wt % | Fluoroalumino silicate glass powder (1) | 32 wt % | | | | |
| | Camphorquinone | 0.2 wt % | Camphorquinone | 1 wt % | | | | |
| | | | N,N-Dimethylaminoethyl methacrylate | 1.5 wt % | | | | |
| Example 15 | 2-Methacryloyloxyethyl dihydrogen-phosphate | 20 wt % | 2-Hydroxyethyl methacrylate | 50 wt % | 15.6 (2.5) | 13.9 (2.7) | 8.9 | 11.6 |
| | 2-Hydroxyethyl methacrylate | 3 wt % | 2-Hydroxy-1,3-dimethacryloxypropane | 10 wt % | | | | |
| | | | Di-2-methacryloxyethyl-2,2,4-trimethylhexamethylene dicarbamate | 10 wt % | | | | |
| | Distilled water | 30 wt % | Distilled water | 10 wt % | | | | |
| | | | Acrylic acid/maleic acid copolymer having | 2 wt % | | | | |

TABLE 1-continued

| Tooth surface conditioning agent | Bonding material | | Adhesive strength [MPa] ( ): Standard deviation | | Released amount of fluoride ion [mg/ml] | |
|---|---|---|---|---|---|---|
| | | | Enamel | Dentin | After 24 hours | After one month |
| Ethyl alcohol<br>Camphorquinone | 46 wt %<br>1 wt % | an average molecular weight of 36,000<br>Fluoroalumino silicate glass powder (1)<br>Camphorquinone<br>Ethyl 4-dimethylaminobenzoate | 15 wt %<br>1 wt %<br>2 wt % | | | |

Comparative Examples 1 to 4

As Comparative Examples, were prepared bonding materials each having a compounding not containing at least one of the acid, the water, and the fluoroalumino silicate glass powder as essential components of the bonding material in the dental adhesive set according to the present invention, acid, water, acid and water, acid and water and fluoroalumino silicate glass powder are not contained in Comparative Examples 1, 2, 3 and 4 respectively, and having the composition and the compounding amount as shown in Table 2. The thus prepared bonding materials were subjected to the same tests as in Examples 1. The results obtained are shown in Table 2.

As is clear from the comparison between the Examples and the Comparative Examples, it has been confirmed that by using the dental adhesive set comprising a tooth surface conditioning agent and a bonding material according to the present invention, a large amount of a fluoride ion is released from the adhesive. It has also been confirmed that the dental adhesive set according to the present invention has a high adhesive strength to a dental restoration against both of an enamel and a dentin and that it enables to achieve restoration with superior adhesive properties through a simple handling.

In the light of the above, the dental adhesive set according to the present invention can firmly and surely adhere a dental restoration to a tooth structure through a clinically simple handling. Also, a reinforcement of tooth structure effect and

TABLE 2

| | Tooth surface conditioning agent | | Bonding material | | Adhesive strength [MPa] ( ): Standard deviation | | Released amount of fluoride ion [mg/ml] | |
|---|---|---|---|---|---|---|---|---|
| | | | | | Enamel | Dentin | After 24 hours | After one month |
| Comparative Example 1 | Citric acid<br>Distilled water<br>Ferric chloride | 15 wt %<br>83 wt %<br>2 wt % | 2-Hydroxyethyl methacrylate<br>Triethylene glycol dimethacrylate<br>Di-2-methacryloxyethyl-2,2,4-trimethylhexamethylene dicarbamate<br>Distilled water<br>Fluoroalumino silicate glass powder (1)<br>Camphorquinone<br>N,N-Dimethylaminoethyl methacrylate | 30 wt %<br>22.5 wt %<br>10 wt %<br>5 wt %<br>30 wt %<br>1 wt %<br>1.5 wt % | 12.3<br>(3.3) | 11.4<br>(3.5) | 0.1 | 0.2 |
| Comparative Example 2 | Citric acid<br>Distilled water<br>Ferric chloride | 15 wt %<br>83 wt %<br>2 wt % | 2-Hydroxyethyl methacrylate<br>Triethylene glycol dimethacrylate<br>Di-2-methacryloxyethyl-2,2,4-trimethylhexamethylene dicarbamate<br>Citric acid<br>Fluoroalumino silicate glass powder (1)<br>Camphorquinone<br>N,N-Dimethylaminoethyl methacrylate | 30 wt %<br>22.5 wt %<br>10 wt %<br>5 wt %<br>30 wt %<br>1 wt %<br>1.5 wt % | 3.0<br>(2.1) | 2.6<br>(1.9) | 5.2 | 6.7 |
| Comparative Example 3 | 2-Methacryloyloxy-ethyl dihydrogen-phosphate<br>2-Hydroxyethyl methacrylate<br>Distilled water<br>Ethyl alcohol<br>Camphorquinone | 20 wt %<br><br>3 wt %<br>30 wt %<br>46 wt %<br>1 wt % | 2-Hydroxyethyl methacrylate<br>2-Hydroxy-1,3-dimethacryloxypropane<br>Di-2-methacryloxyethyl-2,2,4-trimethylhexamethylene dicarbamate<br>Fluoroalumino silicate glass powder (2)<br>Camphorquinone<br>Isoamyl 4-dimethylaminobenzoate | 20.5 wt %<br>25 wt %<br>18 wt %<br>35 wt %<br>0.5 wt %<br>1 wt % | 15.8<br>(3.2) | 16.3<br>(2.8) | 0.1 | 0.2 |
| Comparative Example 4 | 2-Methacryloyloxy-ethyl dihydrogen-phosphate<br>2-Hydroxyethyl methacrylate<br>Distilled water<br>Ethyl alcohol<br>Camphorquinone | 20 wt %<br><br>3 wt %<br>30 wt %<br>46 wt %<br>1 wt % | 2-Hydroxyethyl methacrylate<br>Triethylene glycol dimethacrylate<br>Di-2,-methacryloxyethyl-2,2,4-trimethylhexamethylene dicarbamate<br>Camphorquinone<br>Isoamyl 4-dimethylaminobenzoate | 40 wt %<br>37.5 wt %<br>21 wt %<br>0.5 wt %<br>1 wt % | 16.2<br>(2.9) | 18.1<br>(3.1) | 0 | 0 | inhibition of a secondary caries by an released fluoride ion can be expected, and a stable dental restorative remedy can be realized. Accordingly, the present invention greatly contributes to the dental remedy.

While the invention has been described in detail and with reference to specific embodiments thereof, it will be apparent to one skilled in the art that various changes and modifications can be made therein without departing from the spirit and scope thereof.

What is claimed is:

1. A dental adhesive set comprising (I) a tooth surface conditioning agent and (II) a bonding material, wherein the tooth surface conditioning agent (I) is an acid aqueous solution, and the bonding material (II) comprises a mixture of:

(a) a fluoroalumino silicate glass powder;

(b) one or more polymerizable unsaturated organic compound, having at least one $CH_2=CR_1-COO-$, wherein $R_1$ is H or $CH_3$, and not having an acid group;

(c) an acid selected from the group consisting of at least one of phosphoric acid, hydrochloric acid, citric acid, tartaric acid, malic acid, maleic acid, tricarballylic acid, levulinic acid, pyroglutamic acid, a methacrylate having an acid group and an acrylate having an acid group;

(d) water; and (e) a photopolymerization catalyst.

2. A dental adhesive set as claimed in claim 1, comprising 5 to 70% by weight of the component (a); 25 to 95% by weight of the component (b); 1 to 15% by weight of the component (c); 1 to 15% by weight of the component (d); and 0.1 to 5% by weight of the component (e).

3. A dental adhesive set as claimed in claim 1, wherein the component (a) is a fluoroalumino silicate glass having a mean particle size of 0.02 $\mu$m to 10 $\mu$m and containing $Al^{3+}$, $Si^{4+}$, $F^-$ and $O^{2-}$ as major components and additionally containing $Sr^{2+}$ and/or $Ca^{2+}$.

4. A dental adhesive set as claimed in claim 1, wherein said photopolymerization catalyst comprises a sensitizer and a reducing agent.

* * * * *

UNITED STATES PATENT AND TRADEMARK OFFICE
CERTIFICATE OF CORRECTION

PATENT NO. : 6,217,644 B1
DATED : April 17, 2001
INVENTOR(S) : Matsunae et al.

It is certified that error appears in the above-identified patent and that said Letters Patent is hereby corrected as shown below:

Title page,
Item [30] should read as follows:
[30] Foreign Application Priority Data
Sep. 8, 1998 (JP) ..................................... 10-254037

Signed and Sealed this

Sixth Day of November, 2001

Attest:

*Nicholas P. Godici*

NICHOLAS P. GODICI
*Attesting Officer*   *Acting Director of the United States Patent and Trademark Office*

UNITED STATES PATENT AND TRADEMARK OFFICE
CERTIFICATE OF CORRECTION

PATENT NO.    : 6,217,644 B1
DATED         : April 17, 2001
INVENTOR(S)   : Matsunae et al.

It is certified that error appears in the above-identified patent and that said Letters Patent is hereby corrected as shown below:

Title page,
Item [30], Foreign Application Priority Data, should read as follows:
-- [30]   Foreign Application Priority Data
Sep. 8, 1998     (JP) ................................ 10-254037 --

Signed and Sealed this

Fifth Day of October, 2004

JON W. DUDAS
*Director of the United States Patent and Trademark Office*